United States Patent [19]
Boyle

[11] Patent Number: 6,136,023
[45] Date of Patent: Oct. 24, 2000

[54] WELDED SINUSOIDAL WAVE STENT

[75] Inventor: William J. Boyle, Temecula, Calif.

[73] Assignee: Medtronic, Inc., Minneapolis, Minn.

[21] Appl. No.: 09/136,394

[22] Filed: Aug. 19, 1998

Related U.S. Application Data

[63] Continuation-in-part of application No. 08/633,394, Apr. 16, 1996, abandoned.

[51] Int. Cl.[7] ....................................................... A61F 2/06
[52] U.S. Cl. ......................................... 623/1.22; 623/1.15
[58] Field of Search .............................. 623/11, 12, 1.15, 623/1.16, 1.22, 23.7

[56] References Cited

U.S. PATENT DOCUMENTS

| | | |
|---|---|---|
| 4,649,922 | 3/1987 | Wiktor . |
| 4,856,516 | 8/1989 | Hillstead . |
| 4,878,906 | 11/1989 | Lindemann et al. . |
| 4,886,062 | 12/1989 | Wiktor . |
| 4,994,071 | 2/1991 | MacGregor . |
| 5,019,090 | 5/1991 | Pinchuk . |
| 5,035,706 | 7/1991 | Gianturco et al. . |
| 5,102,417 | 4/1992 | Palmaz . |
| 5,104,404 | 4/1992 | Wolff . |
| 5,133,732 | 7/1992 | Wiktor . |
| 5,135,536 | 8/1992 | Hillstead . |
| 5,195,984 | 3/1993 | Schatz . |
| 5,217,483 | 6/1993 | Tower . |
| 5,282,824 | 2/1994 | Gianturco . |
| 5,304,200 | 4/1994 | Spaulding ................................ 606/198 |
| 5,354,309 | 10/1994 | Schnepp-Pesch et al. . |
| 5,370,683 | 12/1994 | Fontaine . |
| 5,383,887 | 1/1995 | Nadel . |
| 5,405,377 | 4/1995 | Cragg . |
| 5,421,955 | 6/1995 | Lau et al. . |
| 5,443,498 | 8/1995 | Fontaine . |
| 5,449,373 | 9/1995 | Pinchasik et al. . |
| 5,514,154 | 5/1996 | Lau et al. . |
| 5,549,663 | 8/1996 | Cottone, Jr. ................................... 623/1 |
| 5,716,396 | 2/1998 | Williams . |

FOREIGN PATENT DOCUMENTS

| | | |
|---|---|---|
| 0 540 290 A2 | 10/1992 | European Pat. Off. . |
| WO 93/13825 | 7/1993 | WIPO . |

OTHER PUBLICATIONS

Uchida, Barry T., et al. Modifications Of Gianturco Expandable Wire Stents, AJR 150:1185–1187, May 1988.

Wallace, Michael J., et al. Tracheobronchial Tree: Expandable Metallic Stents Used in Experimental and Clinical Applications, Radiology 1986; 158:309–312.

*Applied Vascular Engineering*, Micro Stent Brochure (2 pages).

*Applied Vascular Engineering*, Micro Stent II "The Next Generation" Brochure (2 pages).

*Primary Examiner*—David H. Willse
*Attorney, Agent, or Firm*—Sterne, Kessler, Goldstein & Fox, P.L.L.C.

[57] ABSTRACT

A wire stent having a preformed series of peaks alternating with valleys. The wire is formed from a malleable or resilient material and can be wound into a continuous helix. Each pair of peaks and valleys constitutes a wave. The stent has a number of waves per circumferential revolution such that the adjoining waves align off-peak to off-valley with one or more such adjoining waves being affixed to each other at the off-peak to off-valley locations. The waves can be welded at all locations or only at the circumferential revolutions at the proximal and distal ends of the stent, or intermittently, or in barber pole fashion or along one or more longitudinal axes.

22 Claims, 3 Drawing Sheets

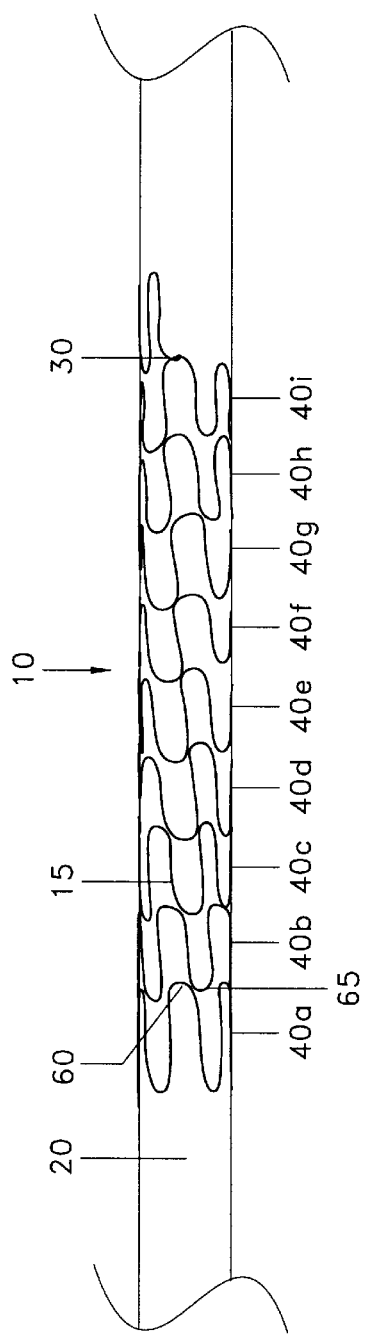

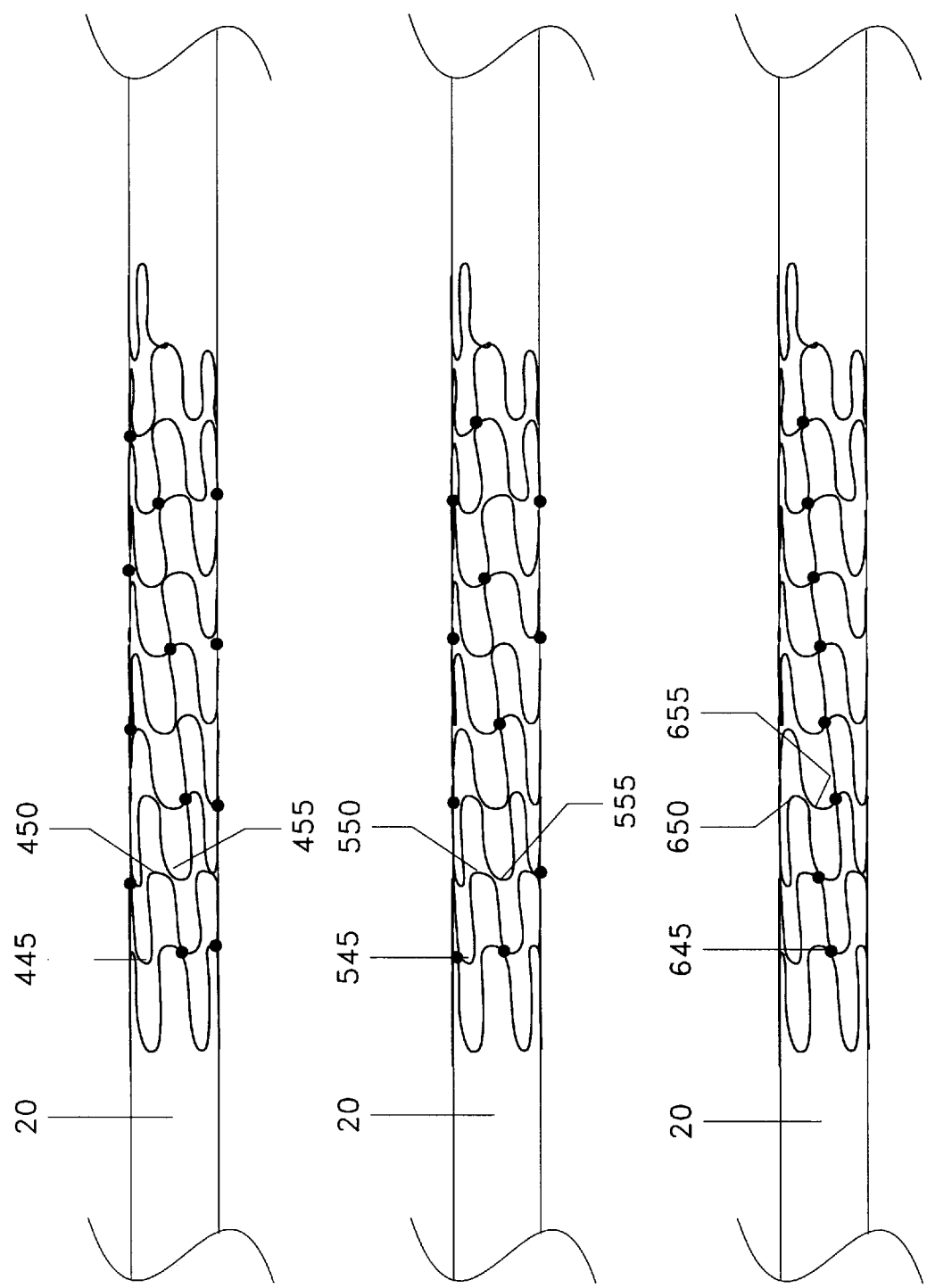

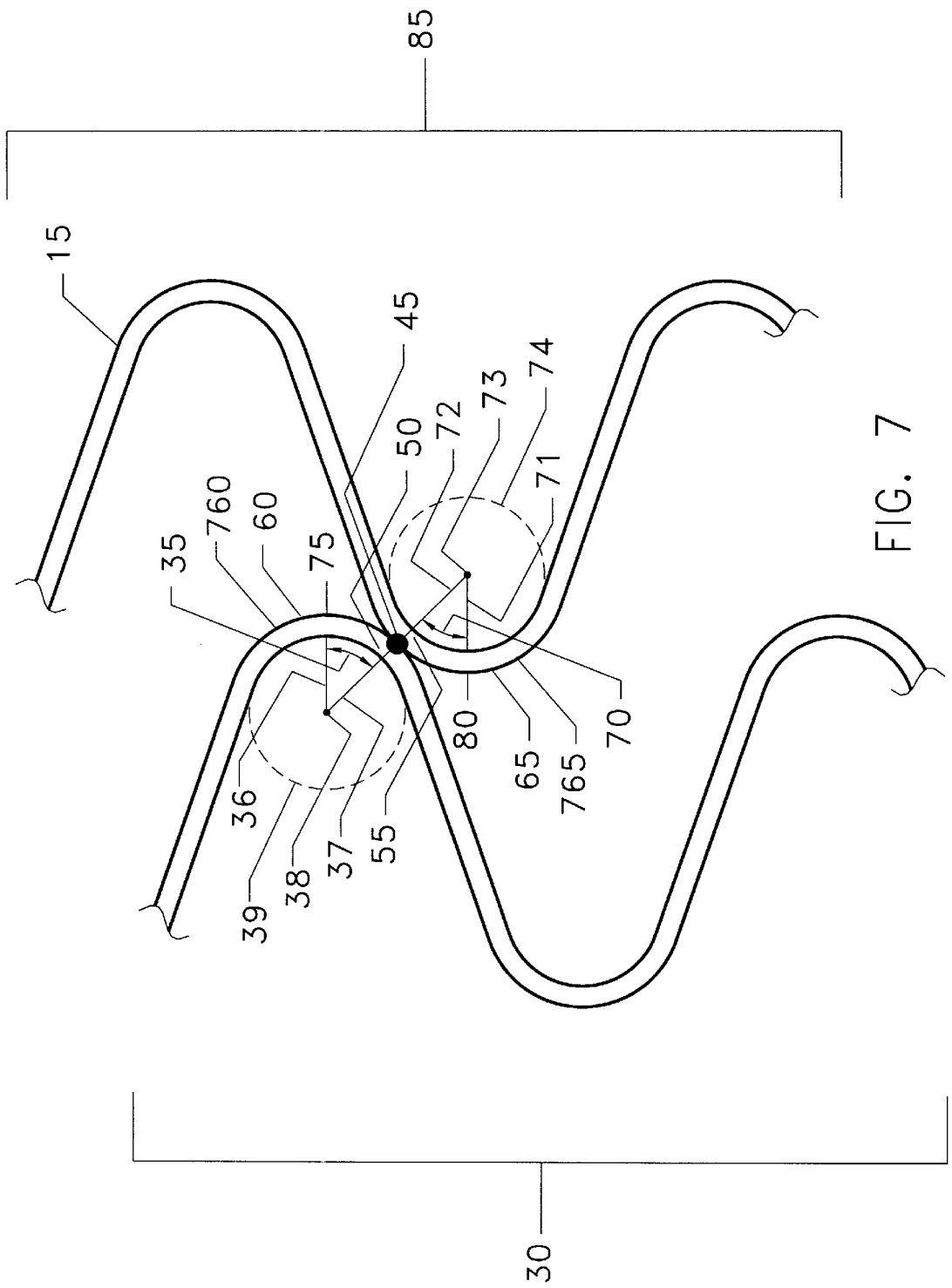

WELDED SINUSOIDAL WAVE STENT

CROSS-REFERENCE TO RELATED APPLICATIONS

This application is a continuation-in-part of Application Ser. No. 08/633,394 filed Apr. 16, 1996, now abandoned.

FIELD OF THE INVENTION

The present invention relates to intravascular stent implants for maintaining vascular patency in humans and animals and more particularly to a stent in the form of a sinusoidal wave which aligns at the off peak to the off valley adjacent locations. A pattern of welds affixes the alignment locations to each other.

BACKGROUND OF THE INVENTION

Percutaneous transluminal coronary angioplasty (PTCA) is used to reduce arterial build-up of cholesterol fats or atherosclerotic plaque. Typically a large guidewire of about 0.038 inches in diameter is steered through the vascular system to the site of therapy. A guiding catheter, for example, can then be advanced over the guidewire to a point just proximal of the stenosis. The large guidewire is then removed. A balloon catheter on a smaller 0.014 inch guidewire is advanced within the guiding catheter to a point just proximal of the stenosis. The guidewire is advanced into the stenosis, followed by the balloon. The balloon at the distal end of the catheter is inflated causing the site of the stenosis to widen. The dilatation of the occlusion, however, can form flaps, fissures and dissections which threaten reclosure of the dilated vessel or even perforations in the vessel wall. Implantation of a metal stent can provide support for such flaps and dissections and thereby prevent reclosure of the vessel or provide a patch repair for a perforated vessel wall until corrective surgery can be performed. Reducing the possibility of restenosis after angioplasty reduces the likelihood that a secondary angioplasty procedure or a surgical bypass operation will be necessary.

An implanted prosthesis such as a stent can preclude additional procedures and maintain vascular patency by mechanically supporting dilated vessels to prevent vessel collapse. Stents can also be used to repair aneurysms, to support artificial vessels as liners of vessels or to repair dissections. Stents are suited to the treatment of any body lumen, including the vas deferens, ducts of the gallbladder, prostate gland, trachea, bronchus and liver. The body lumens range in size from the small coronary vessels to the 28 mm aortic vessel. The invention applies to acute and chronic closure or reclosure of body lumens.

A typical stent is a cylindrically shaped wire formed device intended to act as a permanent prosthesis. A typical stent 10 ranges from 5 mm to 50 mm in length. A stent is deployed in a body lumen from a radially compressed configuration into a radially expanded configuration which allows it to contact and support a body lumen. The stent can be made to be radially self-expanding or expandable by the use of an expansion device. The self expanding stent is made from a resilient springy material while the device expandable stent is made from a material which is plastically deformable, i.e., malleable. A plastically deformable stent can be implanted during a single angioplasty procedure by using a balloon catheter bearing a stent which has been crimped onto the balloon. Stents radially expand as the balloon is inflated, forcing the stent into contact with the body lumen thereby forming a supporting relationship with the vessel walls. Deployment is effected after the stent has been introduced percutaneously, transported transluminally and positioned at a desired location by means of the balloon catheter.

The biocompatible metal stent props open blocked coronary arteries, keeping them from reclosing after balloon angioplasty. A balloon of appropriate size and pressure is first used to open the lesion. The process is repeated with a stent crimped on a second balloon. The second balloon may be a high pressure type of balloon, e.g., more than 12 atmospheres, to insure that the stent is fully deployed upon inflation. The stent is deployed when the balloon is inflated. The stent remains as a permanent scaffold after the balloon is withdrawn.

Various shapes of stents are known in the art. U.S. Pat. No. 4,649,922 to Wiktor for "Catheter Arrangement Having A Variable Diameter Tip and Spring Prosthesis" discloses a linearly expandable spring-like stent. U.S. Pat. No. 4,886,062 to Wiktor for "Intravascular Radially Expandable Stent and Method of Implant" discloses a two-dimensional zig-zag form, typically a sinusoidal form.

U.S. Pat. No. 5,104,404 to Wolff for "Articulated Stent" discloses a stent made up of a number of wires welded together and then connected together with hinges to provide articulation.

U.S. Pat. No. 5,443,498 to Fontaine for "Vascular Stent and Method of Making and Implanting a Vascular Stent" discloses a continuous wire which is formed into a substantially tubular body having a plurality of oblong, open cells which are staggered around the circumference of the tube. When the body is formed in its unexpanded state, the long sides of each oblong cell are arranged substantially parallel to the longitudinal axis of the tubular body. Adjoining cells may then be bonded together at a point between adjacent parallel sides on a cell. The peak apex of one wave is bonded to the adjacent valley apex of the other wave. When the body is expanded, the adjacent sides of each cell extend oblique to the longitudinal axis of the body. See also U.S. Pat. No. 5,370,683 FIGS. 10 and 11 to Fontaine.

U.S. Pat. No. 4,856,516 to Hillstead for "Endovascular Stent Apparatus and Method" discloses a wire first bent into a series of tight bends. The wire is then further bent into a sequence of loops that are connected by half hitch junctions and interconnections which are either aligned or spiral around a circumference of the stent.

U.S. Pat. No. 4,878,906 to Lindemann et al. for "Endoprosthesis for Repairing a Damaged Vessel" discloses a flexible, plastic, thin-walled sleeve molded with various types of circumferential and axial ribs and reinforcements to be used as an endovascular prosthesis.

U.S. Pat. No. 4,994,071 to MacGregor for "Bifurcating Stent Apparatus and Method" discloses a wire forming a backbone extending axially along the length of the lattice that extends away from the lattice and is used to construct the interconnecting loops.

U.S. Pat. No. 5,133,732 to Wiktor for "Intravascular Stent" discloses a stent body coiled from a generally continuous wire with a deformable zig-zag structure with a means for preventing the stent body from stretching along its longitudinal axis.

U.S. Pat. No. 5,304,200 to Spaulding for "Welded Radially Expandable Endoprosthesis and the Like" discloses terminal portions of the end circumferential sections welded directly to a portion of a generally adjacent circumferential section, and the welding preferably is carried out within an inert gas environment in a manner that minimizes crack formation at the weld locations.

SUMMARY OF THE INVENTION

Current continuous wire sinusoidal wave form stents may lack column strength between adjacent waveform wraps which may result in waveform overlap during stent expansion. It is an object of the invention to provide a wire wound stent having good wire coverage and increased column strength as well as to reduce the likelihood of stent wire overlap during stent expansion.

The present invention is accomplished by providing a wire stent having a preformed series of peaks alternating with valleys and wound into a continuous helix having a hollow cylindrical shape. Each peak and valley pair constitute a wave. The stent wire can be fabricated from a malleable or a resilient material. The stent has a number of waves per circumferential revolution such that the adjoining waves align off-peak to off-valley with one or more such adjoining waves being affixed to each other at the off-peak to off-valley locations. The waves can be welded at all locations, or at the circumferential revolutions at the proximal and distal ends of the stent, or intermittently, or in barber pole fashion, or along one or more longitudinal axes.

BRIEF DESCRIPTION OF THE DRAWINGS

FIG. 1 is a top plan view of a stent with four waves per circumferential revolution and without welds;

FIG. 2 is a top plan view of the stent of FIG. 1 with all adjacent waves welded;

FIG. 3 is a top plan view of an the stent of FIG. 1 with the end waves welded;

FIG. 4 is a top plan view of an the stent of FIG. 1 with intermittent waves welded;

FIG. 5 is a top plan view of the stent of FIG. 1 with waves welded in a barber pole configuration;

FIG. 6 is a top plan view of the stent of FIG. 1 with waves welded longitudinally; and FIG. 7 is a top plan view of the stent of FIG. 1 showing an off peak to off valley weld.

DETAILED DESCRIPTION OF THE PREFERRED EMBODIMENTS

Applicant's stent is formed with a wire 15 which is formed into a sinusoidal wave 30 form the length of the stent 10 by a means such as passing the wire through gears such as those disclosed in U.S. Pat. No. 2,153,936 issued to Owens et al. Preferably the wire 15 is wound in a helix pattern around a forming mandrel 20 as in FIGS. 1–6.

A stent can be welded according to the present invention as shown in FIG. 1. This depicts a radially expandable stent 10 in the form of a hollow cylinder defined by a sequence of wire elements 40a–i with each of the wire elements 40a–i extending 360 degrees around the cylinder. The wire elements 40a–i have extendible, sinusoidal zig-zags formed by smooth bends such as alternating peaks 60 and valleys 65. Each peak 60 and contiguous valley 65 pair form a wave 30. As shown in FIG. 7, the peaks 60 and valleys 65 are shaped in a generally longitudinal direction along the cylinder so that the peaks 60 and valleys 65 may open as the wire element 40a is expanded. The wire elements 40a–i are uniformly spaced along the cylinder and the peaks 60 and valleys 65 are uniformly spaced around the cylinder. The adjacent wire elements 40a–i are flexibly connected together in an end-to-end fashion by means of helical winding. The wire elements 40a–i have a plurality of extendible portions, such as peaks 60 and valleys 65 which permit the wire elements to be expanded from a first diameter as seen in FIGS. 1–6 covering 360 degrees of the cylinder to a second, expanded diameter covering 360 degrees of the expanded cylinder.

The wire 15 can have a diameter of 0.001 inches to 0.015 inches. A typical stent 10 ranges from 5 mm to 50 mm in length. The wire elements 40a–i of the stent 10 must expand evenly and permit the balloon to expand evenly. The sinusoidal waves 30 are evenly spaced so that when the stent 10 is expanded the stent 10 will provide even support inside the vessel and resist external loading. A specified and repeatable number of similarly shaped sinusoidal waves 30 in a circumferential cross section are formed from a single length of biocompatible material.

The balloon expandable stent 10 can be made of an inert, biocompatible material with high corrosion resistance that can be plastically deformed at low-moderate stress levels such as tantalum, the preferred embodiment. Other acceptable materials include nickel titanium, stainless steel, titanium ASTM F63-83 Grade 1, niobium or high carat gold K 19–22. A self-expanding device can be made by the use of superelastic NiTi such as nitinol manufactured by Raychem or Forukawa.

A forming mandrel sequence can provide a gradual reduction in the stent 10 outer diameter by the use of finger pressure under microscopic observation. For a coronary sized stent it is possible to go directly from a 0.150 inch stent outer diameter to a 0.065 inch stent outer diameter by placing stent 10 directly onto the balloon from the forming mandrel 20 and make an acceptable stent, but it is more difficult to maintain proper alignment of the stent 10 wires by doing so. Thus it is preferred that the stent 10 is further processed from a 0.150 inch diameter forming mandrel by pressing it onto a 0.100 inch diameter forming mandrel, thereafter pressing it onto a 0.080 inch diameter forming mandrel and finally pressing it onto a 0.065 inch diameter forming mandrel before being applied to the balloon. Those skilled in the art would recognize that a variety of acceptable mandrel sizes could be used in the forming sequence depending on the desired stent size.

The stent may terminate at the distal end and the proximal end with an end attachment 25 as seen in FIG. 1. After the stent 10 has been reduced to the objective outer diameter, the proximal and distal ends of the wire 15 are manually looped around the nearest adjacent wave. When four, five or six waves per helical revolution are used, the proximal and distal ends of the wire 15 can be looped to the fourth, fifth or sixth respective wave back from either end of the wire 15. Those skilled in the art will recognize other means of end attachments which may include twisting, biocompatible adhesive, brazing, crimping, welding or stamping.

The stent 10 is removed from the mandrel and placed over a suitable expandable diameter device such as an inflatable balloon which is typically used for angioplasty procedures. The stent 10 is centrally located and positioned with respect to the length of balloon. A stent 10 can be implanted during a single angioplasty procedure by using a balloon catheter bearing a stent 10 which has been crimped on by hand or with a suitable crimping tool (not shown) onto the balloon. Manually squeezing the stent 10 over the balloon is also acceptable. As the balloon expands, so does the stent 10. The expanding balloon together with the stent 10 compresses the plaque in the stenosis and prevents possible reocclusion. When the angioplasty procedure is completed, the balloon is deflated and withdrawn leaving the stent 10 firmly implanted within the vessel. The previously occluded vessel is recannalized and patency is restored.

Using a 0.005 inch diameter wire to make a coronary-sized stent, the sinusoidal wave 30 of the present invention can have a wave length of about 0.150 inches to 0.090 inches and a wave amplitude of about 0.050 inches to 0.080 inches. The sinusoidal wrap angle is approximately 10 degrees to 15 degrees from a transverse orientation with respect to the forming mandrel 20. With these dimensions, between 4 and 6 waves per circumferential revolution will occur. For 4 waves per circumferential revolution, a wave amplitude of 0.057 inches +/−0.005 inches and a wave length of 0.098 inches +/−0.003 inches may be used.

With approximately 5 waves per circumferential revolution of the preferred dimension for a coronary stent, the continuous sinusoidal waveform wraps around the mandrel 20 such that the waveform peak apex 75 and valley apex 80 sections align. With approximately 4 waves per circumferential revolution of the preferred dimension, the continuous sinusoidal waveform wraps around the mandrel such that the waveform sections align off-peak to off-valley in a partially nested fashion, as shown in FIG. 7. Welding off-apex provides a greater area on which to weld because the curve is not as sharp at that point and provides a surface of greater contact.

Off-peak refers to a location on a peak on either side of the peak apex. Preferably, off-peak comprises an off-peak point on a wave indicated by a peak angle of greater than 0 degrees and not greater than 90 degrees. As shown in FIG. 7, the peak angle 35 is established relative to the curvature of the peak 760 at the peak apex 75. The dashed circle 39 defines the curvature of the arc that characterizes peak 760; it is included in FIG. 7 solely to illustrate the geometry of the off-peak to off-valley contact between waves 30 and 85 and is not itself a structured component of the stent. The peak angle 35 is the angle between a line 36 drawn perpendicular to, and passing through, the peak apex 75, and a line 37 passing through the off-peak point 50 on the wave 30, each of which passes through the center 38 of the circle 39. That is, the center 38 of the circle 39 functions as the vertex of the peak angle 35.

Likewise, off-valley refers to a location on a valley on either side of the valley apex. Preferably, off-valley comprises an off-valley point on a wave indicated by a valley angle of greater than 0 degrees and not greater than 90 degrees. As shown in FIG. 7, the valley angle 70 is established relative to the curvature of the valley 765 at the valley apex 80. The dashed circle 74 defines the curvature of the arc that characterizes valley 765; it is included in FIG. 7 solely to illustrate the geometry of the off-peak to off-valley contact between waves 30 and 85 and is not itself a structural component of the stent. The valley angle 70 is the angle between a line 71 drawn perpendicular to, and passing through, the valley apex 80, and a line 72 passing through the off-valley point 55 on the wave 85, each of which passes through the center 73 of the circle 74. That is, the center 73 of the circle 74 functions as the vertex of the valley angle 70.

Preferably the weld 45 is at a contact point comprising an off-peak point 50 indicated by a peak angle 35 of 45 degrees and an off-valley point 55 indicated by a valley angle 70 of 45 degrees.

At 5 or 6 waves per circumferential revolution of a coronary stent, metal mass increases resulting in more radial hoop strength at the center of the stent than at the ends. The greater the number of waves, the greater the hoop strength at the center of the stent. This can result in the balloon expanding first at the distal and proximal ends before expanding at the center of the stent which creates a "dumb bell" shaped balloon. With the stent ends expanding first, the stent slides down the expanded balloon ends toward the center of the balloon which is as yet unexpanded because of the stent's increased radial hoop strength in the center. This results in uneven expansion of the balloon. Increased metal mass also results in stiffening in the longitudinal direction. Four waves per circumferential revolution is therefor preferred.

It is desirable to join wave sections to increase column or longitudinal strength/rigidity/support to both the unexpanded and expanded stent structure. Joining wave sections also reduces the likelihood of adjacent wave 30 overlap during the crimping of the stent 10 onto a delivery system as well as preventing adjacent wave 30 overlap during stent expansion. Wave overlap is undesirable because the overlapping elements 40 may project down into the luminal flow causing turbulence in the blood flow. This may cause blood clot formation which may lead to further medical complications. Joining wave 30 sections also provides a more consistent and uniform expanded stent length and geometry.

Given the natural off-apex alignment of four waves per circumferential revolution of applicant's stent of the preferred dimension supra, the off-peak point 50 can be joined with the adjacent off-valley point 55 as seen in FIG. 7 by stamping, brazing, adhesive bonding, biocompatible connection or welding such as resistance welding and most preferably by laser welding. The same stent configuration could also be formed by chemically etching or laser cutting from a small diameter tubing.

Laser welding is the preferred method of joining adjacent wave sections because it minimizes the effect of mechanical degradation of the wire 15 by localizing the delivery of heat to a relatively small region. Suitable welding settings include a power setting of 4 Hz, a pulse width of 0.6 mSec., a charge voltage of 200, joules/pulse of 0.13 with a 200 micron filter and a 100 mm focusing lens. The stent 10 is placed on a fixture such as a mandrel 20 to hold the waves in contact with each other. An inert gas is used such as argon or helium to flood the weld area. The flow rate of the gas must be sufficient to prevent oxidation by excluding gasses that would oxidize and embrittle the weld.

There are multiple suitable welding configurations using four sinusoidal waves per revolution. In the first embodiment shown in FIG. 2, all adjacent waves could have welds 245 at the adjacent off-peak 250 and off-valley 255 locations. This would produce a relatively stiff stent in the longitudinal direction.

In the second embodiment which is shown in FIG. 3, the waves are welded at the adjacent off-peaks 350 and off-valleys 355 at the proximal and distal ends of the stent. One or more, preferably not more than two circumferential revolutions of elements 340a, b, h, and i at the proximal and distal ends could have such welds 345. Those waves comprising the center portion of the stent such as 340e are unjoined for improved longitudinal flexibility.

In the third embodiment seen in FIG. 4, the adjacent off-peak 450 and off-valley 455 wave segments may be welded 445 intermittently along the length of the longitudinal axis of the stent, as for example, every other wave intersection. The intermittent welds 445 increase longitudinal flexibility over that of the fully welded stent of FIG. 2

In the fourth embodiment seen in FIG. 5, adjacent waves may have welds 545 in a spiral barber pole effect. The advantage of the barber poll effect is that it prevents overlap of adjacent wire in the expanded stent.

In the fifth embodiment seen in FIG. 6, adjacent off-peak 650 and off-valley 655 waves may have welds 645 along a longitudinal axis parallel to the longitudinal axis of the mandrel 20. There can also be a second longitudinal series of welded waves at 180 degrees from the first longitudinal series. The longitudinal series of welds 645 prevents overlap of adjacent wire in the expanded stent.

The preceding specific embodiments are illustrative of the practice of the invention. It is to be understood, however, that other expedients known to those skilled in the art or disclosed herein, may be employed without departing from the scope of the appended claims.

| No. | Component |
|---|---|
| 10 | Stent |
| 15 | Wire |
| 20 | Mandrel |
| 25 | End Attachment |
| 30 | Wave |
| 35 | Peak Angle |
| 40, 340 | Element |
| 45, 245, 345, 445, 545, 645 | Weld |
| 50, 250, 350, 450, 550, 650 | Off-Peak |
| 55, 255, 355, 455, 555, 655 | Off-Valley |
| 60 | Peak |
| 65 | Valley |
| 70 | Valley Angle |
| 75 | Peak Apex |
| 80 | Valley Apex |
| 85 | Wave |

What is claimed is:

1. A medical device for use in supporting a luminal surface of a human or animal body comprising a malleable or resilient wire having a proximal end, a distal end, and a preformed series of peaks alternating with valleys; each peak and contiguous valley constituting a wave; the device being formed in a hollow cylindrical shape comprising a plurality of circumferential revolutions of the wire and having a number of waves per circumferential revolution; wherein a first wave of a circumferential revolution having an off-peak point aligns to a second wave of an adjoining circumferential revolution having an off-valley point and wherein the first and second waves of at least one pair so aligned are affixed to each other at a contact point comprising the off-peak point of the first wave and the off-valley point of the second wave.

2. The medical device according to claim 1 wherein the first and second waves are welded to each other at the contact point.

3. The medical device according to claim 2 wherein the first and second waves are laser welded to each other at the contact point.

4. The medical device according to claim 1 wherein the off-peak point is defined by a peak angle of greater than 0 degrees and not greater than 90 degrees and wherein the off-valley point is defined by a valley angle of greater than 0 degrees and not greater than 90 degrees.

5. The medical device according to claim 4 wherein the peak angle comprises 45 degrees and the valley angle comprises 45 degrees.

6. The medical device according to claim 1 wherein the wire is made of a biocompatible metal that can be plastically deformed at low to moderate stress levels.

7. The medical device according to claim 1 wherein the wire is formed of a super-elastic metallic material.

8. The medical device according to claim 1 wherein the wire has four waves per circumferential revolution.

9. The medical device according to claim 1 wherein each first wave and each second wave are welded to each other at each and every contact point.

10. The medical device according to claim 1 wherein the proximal end of the wire and the distal end of the wire each comprises at least one contact point at which a first and second wave are affixed.

11. The medical device according to claim 10 wherein the proximal end of the wire and the distal end of the wire each comprises at least one first circumferential revolution, each wave of the first circumferential revolution having an off-peak point that aligns to a wave of a second adjoining circumferential revolution having an off-valley point and wherein each of the waves of the first circumferential revolution is affixed to a wave of the second circumferential revolution at a contact point comprising an off-peak point of a wave of the first circumferential revolution and an off-valley point of a wave of the second circumferential revolution; the wire further comprising at least one third circumferential revolution between the proximal and distal ends of the wire, each wave of the third circumferential revolution being unaffixed to a wave of an adjoining circumferential revolution.

12. The medical device according to claim 1 wherein pairs of first and second waves so aligned are welded intermittently throughout the helix.

13. The medical device according to claim 1 wherein pairs of first and second waves so aligned are welded in a spiral barber pole fashion relative to the longitudinal axis of the cylinder.

14. The medical device according to claim 1 wherein the pairs of first and second waves so aligned are welded along one or more longitudinal axes of a helix parallel to the longitudinal axis of the cylinder.

15. The medical device of claim 1 wherein the wire is wound into a continuous helix.

16. A medical device for use in supporting a luminal surface of a human or animal body comprising a malleable or resilient wire having a proximal end, a distal end, and a preformed series of peaks alternating with valleys; each peak and contiguous valley constituting a wave; the device being formed in a hollow cylindrical shape comprising a plurality of circumferential revolutions of the wire and having a number of waves per circumferential revolution; wherein a first wave of a circumferential revolution having an off-peak point aligns in a partially nested fashion to a second wave of an adjoining circumferential cicumferential revolution having an off-valley point and wherein the first and second waves of at least one pair so aligned are affixed to each other at a contact point comprising the off-peak point of the first wave and the off-valley point of the second wave.

17. The medical device according to claim 16 wherein the first and second waves are welded to each other at the contact point.

18. The medical device according to claim 16 wherein the off-peak point is defined by a peak angle of greater than 0 degrees and not greater than 90 degrees and wherein the off-valley point is defined by a valley angle of greater than 0 degrees and not greater than 90 degrees.

19. The medical device according to claim 18 wherein the peak angle comprises 45 degrees and the valley angle comprises 45 degrees.

20. The medical device according to claim 16 wherein the wire has four waves per circumferential revolution.

21. The medical device according to claim 16 wherein the proximal end of the wire and distal end of the wire each comprises at least one contact point at which a first and second wave are affixed.

22. The medical device according to claim 16 wherein the wire is wound into a continuous helix.

* * * * *